(12) United States Patent
Olsson et al.

(10) Patent No.: US 8,292,823 B2
(45) Date of Patent: Oct. 23, 2012

(54) SYSTEM AND METHOD FOR DIAGNOSIS OF BRAINSTEM DISORDERS

(75) Inventors: Olle Olsson, Lund (SE); Sören Nielzén, Lund (SE); Sara Fristedt Nehlstedt, Lund (SE); Johan Källstrand, Lund (SE)

(73) Assignee: SensoDetect Aktiebolog, Lund (SE)

( * ) Notice: Subject to any disclaimer, the term of this patent is extended or adjusted under 35 U.S.C. 154(b) by 1161 days.

(21) Appl. No.: 11/759,871

(22) Filed: Jun. 7, 2007

(65) Prior Publication Data

US 2007/0299359 A1   Dec. 27, 2007

(51) Int. Cl.
*A61B 5/00* (2006.01)

(52) U.S. Cl. ........................ 600/559; 600/544

(58) Field of Classification Search ............... 600/300, 600/301, 544, 545, 558, 559
See application file for complete search history.

(56) References Cited

U.S. PATENT DOCUMENTS

| | | | |
|---|---|---|---|
| 4,421,122 A | 12/1983 | Duffy | |
| 5,003,986 A | 4/1991 | Finitzo et al. | |
| 5,370,126 A | 12/1994 | Clifford, Jr. | |
| 5,891,050 A | 4/1999 | Gänsler et al. | |
| 5,954,667 A | 9/1999 | Finkenzeller et al. | |
| 6,200,273 B1 | 3/2001 | Sininger et al. | |
| 2005/0085744 A1* | 4/2005 | Beverina et al. | 600/558 |
| 2007/0106169 A1* | 5/2007 | Fadem | 600/544 |

FOREIGN PATENT DOCUMENTS

| | | |
|---|---|---|
| BY | 5526 C1 | 9/2003 |
| DE | 32 19 469 A1 | 11/1983 |
| RU | 95110924 A1 | 7/1997 |
| UA | 54271 A | 2/2003 |
| WO | WO 2004/112604 A2 | 12/2004 |
| WO | WO 2004112604 A2 | 12/2004 |

OTHER PUBLICATIONS

Russian Patent and Trademark Office, Office Action in Application No. 2007125657/14(027951) dated Aug. 11, 2010, with translation, 5 pages.
European Patent Office, Search Report in Application Number 05813532.8-1526/1824384 (PCT/SE2005/001877) dated Jul. 6, 2010, 7 pages.

(Continued)

*Primary Examiner* — Max Hindenburg
*Assistant Examiner* — Jonathan M Foreman
(74) *Attorney, Agent, or Firm* — Inskeep IP Group, Inc.

(57) ABSTRACT

A system and method for detection of a brainstem disorder, such as schizophrenia, using brainstem audiometry, is disclosed. A subject's (4) responses on the physical properties of sound, such as frequency, time and amplitude, are being detected. Sound stimuli are being presented, via a communication element (2) through a hearing organ (3) to the subject. Elements (7) are attached to the subject (4) for measurement of the subject's electrophysiological brain activity. Simultaneously as the mentioned sound stimuli (1) are presented to the subject (4) a trig signal is sent out from the organ for generation of stimuli (1), via a trig box (5), further to an organ for registration (6) of the electrophysiological brain activity in the subject (4), whereafter the electrophysiological brain activity is stored and imaged in computer equipment (8) for determination of a brainstem disorder in the subject.

13 Claims, 5 Drawing Sheets

OTHER PUBLICATIONS

Nielzén, S. et al., "Klinisk psykoakustik kan ge objektiv diagnos vid schizofreni," *Läkartidningen* [in Swedish, no translation available] Nr 15-16, Volym 101, 2004, 4 pages.

Zenkov, L.P. et al., "Induced Auditory Brainstem Potentials," *Functional Diagnostics of Diseases of Nervous System* [in Russian, no translation available], M., Medicine, 1991, pp. 241-251.

The State Committee for Science and Technologies of the Republic of Belarus, National Center of Intellectual Property, Decision to Grant in Belarus Patent Application No. a20070841 issued Nov. 16, 2011 (with translation), 13 pages.

* cited by examiner

14.

15.

20.

SYSTEM AND METHOD FOR DIAGNOSIS OF BRAINSTEM DISORDERS

RELATED APPLICATIONS

This application claims priority to International Application No. PCT/SE2005/001877 filed Dec. 8, 2005 entitled System And Method For Diagnosis Of Brainstem Disorders, and to Swedish Patent Application No. 0402998-9 filed Dec. 8, 2004 entitled Anordning Och Metod För Psykoakustisk Diagnostic Av Schizofreni, now Swedish Patent No. SE 527 967 C2, both of which are hereby incorporated by reference.

BACKGROUND OF THE INVENTION

The present invention pertains to a system for diagnosis of brainstem disorders, such as schizophrenia, and particularly to a method of using said system in respect of diagnosis of brainstem disorders, such as schizophrenia.

Disorders of the nervous system are a growing concern. One area of nervous disorders are brainstem disorders. One such disorder is schizophrenia—a hereditary disease—which is a disruption in the nerve transmission within and between all systems in the nervous system which handle the electrical representation of the tactile sense, vision, hearing, thinking and motor functions. The origin of the disease is hitherto unknown.

Today there are no established, objective measures for determining schizophrenia. Clinical diagnostics, which means clinical observation and evaluation of the patient's symptoms is most commonly used to diagnose schizophrenia.

Psychological tests are being used, but these measure general functions which are not specific for schizophrenia. A vast number of visual and psychological tests of perception are described in the literature but these are solely of scientific interest and are not being used clinically. Furthermore, no tests available today have sufficiently predictive abilities regarding schizophrenia.

By using several psychological functioning tests a prediction for schizophrenia at below 70% can be achieved. This means that in 70% of the cases the schizophrenic-typical test results leads to a diagnosis later. Thus the specificity is still rather uncertain.

Diagnostic methods at hand today are very time consuming. Regarding forensic psychiatry a process of at least 30 working days and an investigation team comprising at least six professionals is needed to set a more reliable diagnosis. Admissions with months of observations and investigations are common procedure and sometimes the diagnosis can be established only after years of follow-ups in the non-institutional care. In conclusion, today diagnoses are established by means of traditional psychiatric observation, a time consuming process which leads to a much more severe disease. Thus, with today's diagnostic methods it is most frequently too late for efficient therapeutic treatment.

Organic alterations, today measurable by means of neuro-imaging techniques, reflect late physiological effects of the disease. The psychological cognitive tests that are being used in diagnostics measure frontal lobe dysfunction and word-tests indicate temporal lobe dysfunction, which both are late processes too. Psychological tests are more aimed at diagnosing dementia than schizophrenia.

Electrophysiology can give some information for example by means of P300. P300 is a positive wave in the electroencephalogram (EEG) which correlates with a large number of repeated stimuli presented through the hearing or visual modalities. It is claimed to be an expression of the nervous system's regulation of attentiveness. However, the variation within this measure obtained is far too large to obtain diagnostic reliability for schizophrenia and the need of more precise instruments for diagnostic purposes is acute. To obtain an objective measure on the early schizophrenia, specific stimulation and ascertained correlation between the results and other diagnostic measures of the disease are needed. The majority of patents regarding schizophrenia are based on biochemical and genetic models and practically oriented clinical test is not disclosed.

In patent WO-AI-03026500 a psycho-physiological test for diagnosis of schizophrenia is disclosed. The document describes a device and method for measurement of binochular rivalry. This psycho-physiological test demands the subject's active participation as reflected by decision-making and pushing a button, and thus it cannot be regarded being truly physiologically objective. This issue is of uttermost importance, since it might interfere with the perceptual process.

The state of the art refers to the usage of simple sound stimulation, such as click trains, with identical click or pulse trains with isolated differing pulses, whereby the brain reaction to difference is recorded, to obtain electrophysiological brain (cortex) reading in respect of schizophrenia diagnosis. This is called MMN (MisMatch Negativity). The time span used in MMN is in the interval 80 to 300 ms.

U.S. Pat. No. 5,954,667 discloses a device for derivation of acoustically evoked brain potentials. The triggering mentioned in U.S. Pat. No. 5,954,667 concerns the generation of a sequence of clicks when the device is activated by a finger operable switching action. Therefore, the measurement of brain activity occurs during a longer time and not simultaneously as the sound stimulation. Every click sound in U.S. Pat. No. 5,954,667 does not release a new reading of brain activity. Therefore, the device according to U.S. Pat. No. 5,954,667 is not capable of detecting, and diagnosing, brain disorders, such as schizophrenia, but only capable of controlling the hearing in subjects, such as a child, incapable of actively responding to sound stimuli.

Other documents disclosing the state of the art are the two articles; "Novelty-elicited mismatch negativity in patients with schizophrenia on admission and discharge", Journal of Psychiatry & Neuroscience, vol 26, nr 3, 2001, pages 235 to 246; and Nisad, Schizophrenia Research, Research News, March 2003.

Hence, an improved system, and a method thereof, for diagnosis of brainstem disorders, such as schizophrenia, would be advantageous and in particular a system allowing for a testing procedure that does not rely on any cognitive effort from the subject would be advantageous. Also, specificity and reliability of the diagnosis should be more advantageous.

OBJECTS AND SUMMARY OF THE INVENTION

Accordingly, the present invention preferably seeks to mitigate, alleviate or eliminate one or more of the above-identified deficiencies in the art and disadvantages such as the above-identified, but not limited to, singly or in any combination and solves the above mentioned issues such, but not exclusively limited to these issues, by providing systems, and methods according to the appended patent claims.

BRIEF DESCRIPTION OF THE DRAWINGS

These and other aspects, features and advantages of which the invention is capable of will be apparent and elucidated from the following description of exemplary embodiments of the present invention, reference being made to the accompanying drawings in which.

Figure 1:
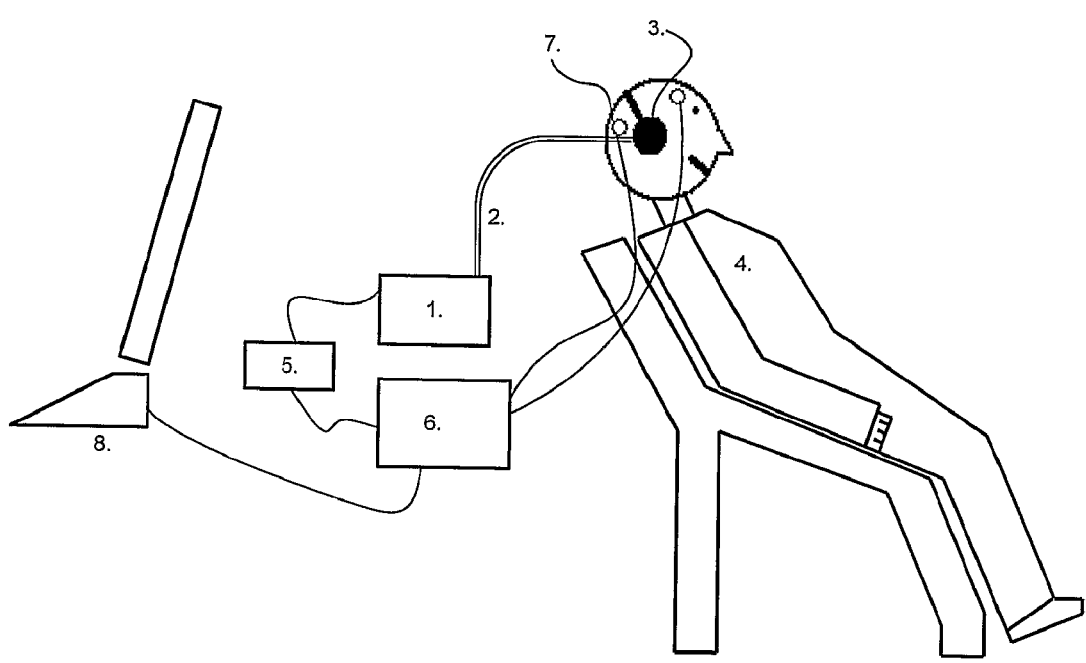
FIG. 1 is a schematic illustration of a system according to one embodiment of the present invention.
Figure 2:
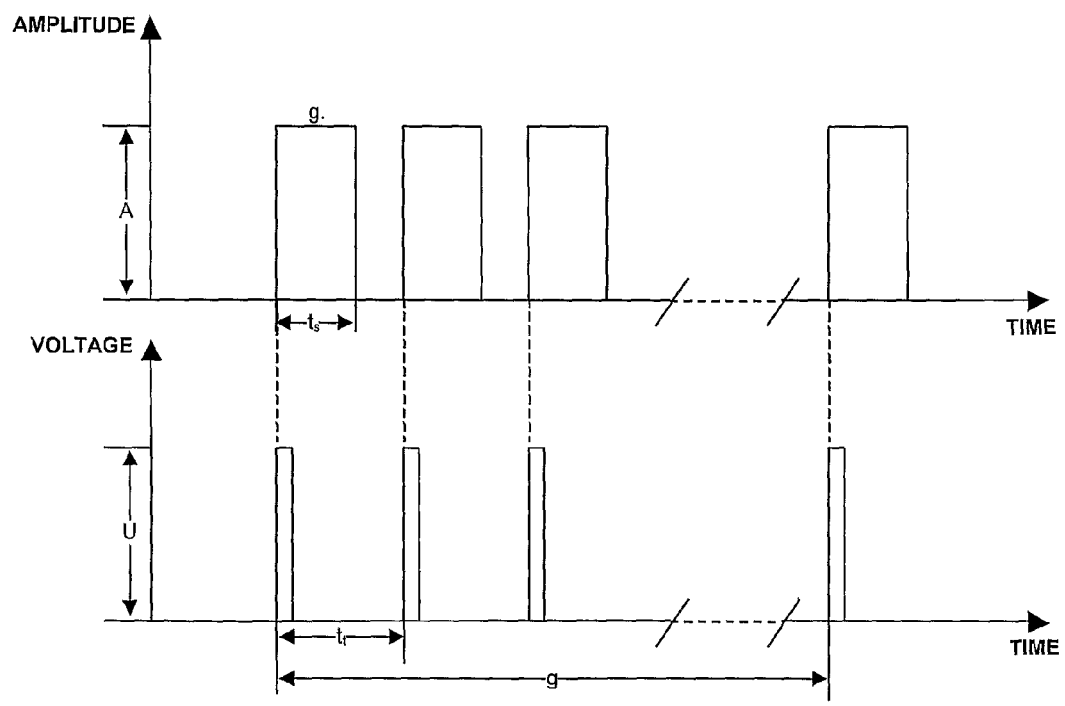
FIG. 2 is a timing diagram that presents common features, as for instance for nine tests in one embodiment of the present invention.
Figure 3:
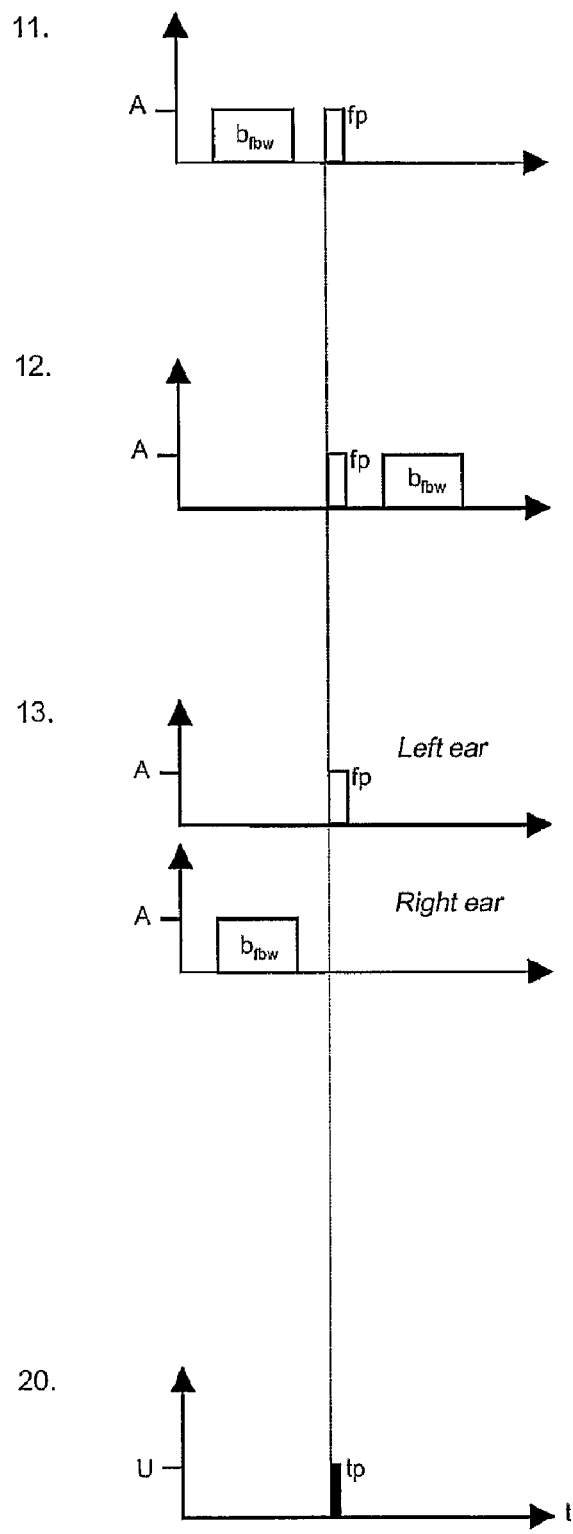
FIGS. 3, 4 and 5 are schematic illustrations and diagrams that further illustrate the nine test's sound stimuli according to one embodiment of the present invention.
Figure 4:
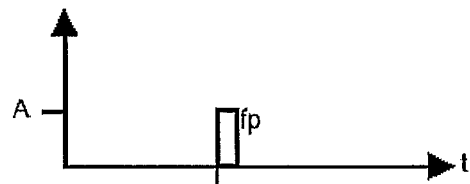
Figure 4:
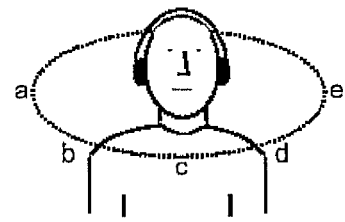
Figure 4:
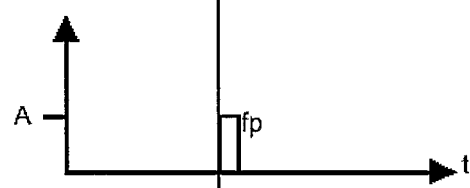
Figure 4:
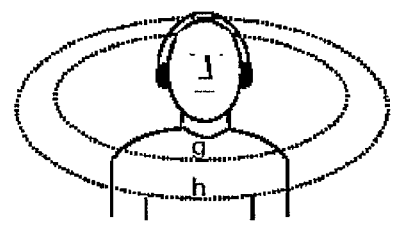
Figure 4:
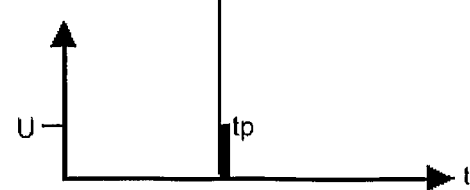
Figure 5:
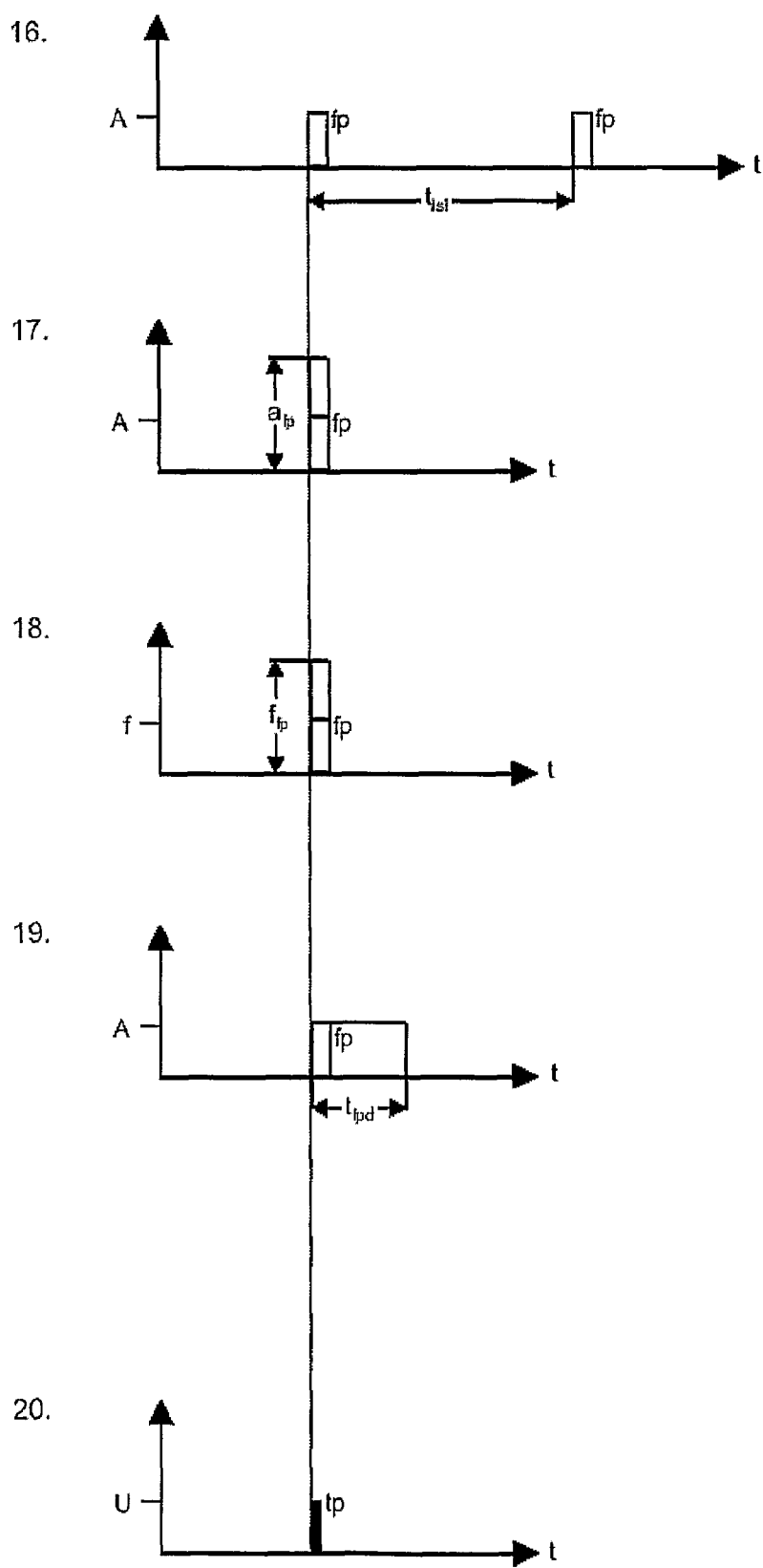

Abbreviations used in FIGS. 1 to 5:
A=The amplitude of the sound stimuli
U=The voltage of the trigger pulse
Tt=Time between the trig pulses
Ts=The duration of sound stimuli
G=Number of repetitions of the stimuli for a test
Sssp=square-shaped sound pulse (fp)
B fbw=Butterworth filtered white noise
T isi=Time between square-shaped sound pulses for test 16
A fp=The amplitude variation for the square-shaped sound pulses for test 17
f=The frequency for the reference square-shaped sound pulse for test 18
f fp=The frequency variation for the square-shaped sound pulse for test 18
t fpd=The duration variation for the square-shaped sound pulse for test 19

DETAILED DESCRIPTION OF THE INVENTION

The present invention comprises a system and a method intended for diagnosis and/or therapeutic control of brains stem disorders, such as schizophrenia. In this aspect the system and method thereof, comprise means of auditory brainstem audiometry.

The present invention is not intended to be limited to diagnosis and/or control of schizophrenia, even though schizophrenia is mentioned in the embodiments of the present invention. Rather, the present invention includes the diagnosis and/or therapeutic control of all disorders assignable to brainstem related disorders.

By using the physical properties of sound; frequency, time and amplitude, and the knowledge that these three properties, or combinations of these, is treated in different networks in the brain, a number of specific subtests have been created, which have been proven to separate schizophrenic subjects from psychiatrically healthy reference subjects. More specifically this is achieved by letting the subject undergo a test, comprised of a number of subtests. During the test procedure electrophysiological signals from the brain stem are registered, which reflect the different sound stimuli and furthermore the results are stored, analyzed and interpreted. The final result is a profile of the brainstems audio-physiological functioning.

Both the composition of the sound stimuli and the method of analyzing the schizophrenia-specific electrophysiological response pattern, are new methodological concepts which makes identification of the early stages in brains stem related diseases, such as schizophrenia, possible, which in turn facilitates efficient treatment with adequate therapeutic resources in time.

The present invention at hand does not rely on any cognitive effort from the subject during the testing procedure. The test is automated, and does not need the active contribution of the test object. Furthermore, the technique has never before been used for psychiatric diagnostic purposes.

Audiometry has been used for examination and as a diagnostic instrument of organic conditions in the central nervous system, e.g. measurement of hearing thresholds in infants and for subjects who not are able to be tested with routine audiogram. However, it has not been use for diagnosing of brainstem related diseases. Brainstem audiometry is characterized by an electrophysiological imaging method of the brainstems coding during stimulation with different sound sequences.

In one embodiment, according to FIG. 1, the system according to the present invention comprises an apparatus for generation of stimuli (1), such as a tone generator according to the present embodiment, by means of which the aforementioned sound stimuli are being presented, via a communication element (2), such as a plastic hose, cord or an electric cable, and a sound generating device (3), such as a hearing phone, to a subject (4). A plastic hose has the advantage that it does not generate electromagnetic fields near the test subject, which may interfere with brainstem activity or the measurements thereof.

Simultaneously as the sound stimuli are being presented, a trig-pulse is being emitted from the system for generation of stimuli (1) to a triggering device (5), such as a trig-box, and further on to an apparatus for analysis and storage of information (6), such as brainstem activity, in which registration of electrophysiological brain activity from electrodes (7) is initiated, whereafter the activity is imaged on an equipment (8), such as a computer equipment. The triggering of registration is hence initiated by each start of a stimuli.

This system may, in one embodiment of the present invention, be used to perform a test-battery for schizophrenia consisting of nine tests, in which each test comprises presentation of stimuli to a subject and registration of the response elicited by mentioned sound stimuli. Common features for the nine tests are that the sound stimuli being presented to the subject are presented in repeated sequences; typically sound stimuli are repeated approximately 500-1500 times and the time between stimuli varies from approximately 150 to 500 ms. Hence, a complete test with high reliability is provided that takes some minutes, compared to weeks according to the prior art. Because of the fact that each stimulation is registered when the trig-pulse initiates the imaging apparatus, the brain activity caused by the stimulation appears more significantly on a continuous basis in relation to other brainstem activity. In this way the brainstems specific responses to stimuli are registered. The recorded electrophysiological responses from the subject are thereafter compared with standardized responses from a reference population.

The present invention differs among other things from the prior art in that the apparatus for generation of stimuli (1) is configured to transmit, or send, a triggering signal, via and/or through the triggering device (5), to the apparatus for analysis and storage of information (6) of the electrophysiological brain activity simultaneously as said sound stimuli is transmitted to the subject (4) from the apparatus for stimuli generation (1).

Therefore, the present invention uses according to some embodiments auditory brainstem response (ABR) to detect brain disorders, such as schizophrenia.

The term "auditory brainstem response" is commonly used to define electrophysiological measurement of the activity of the brainstem within a time span of 0 to approximately 10 ms. Of course this time span may vary somewhat, but not principally deviate from this time span, while still be inside the scope of the present invention, according to the appended claims.

The present invention comprises triggering of brainstem reading in relation to complex sound sequences, which are specifically developed for diagnostic and detecting purposes regarding brain disorders, such as schizophrenia. Hereby, the present invention comprises triggering in respect of sound experiencing mechanisms and not general neurological phenomena, such as detection of difference. Thus, the triggering according to the present invention is inseparable from the complex sound stimuli, presented herein.

Some of the tests in the present invention are based on auditory masking. Masking is defined as the subjects reduced ability to hear one sound in the presence of another sound presented simultaneously, before or after the sound one are trying to hear. These processes are handled by general coding principles within the nervous system. Information is sorted and rudimentary parts of it are damped or filtered away. This is made out by feedback-mechanisms in the nervous system which facilitates or inhibits impulses. Said sorting is handled by priority or down-regulation between different mechanisms, working more or less independently of each other.

Furthermore, directional hearing is investigated, which refers to the ability of spatial location of sounds. Both left/right—ability and coding of distance are investigated. Left/right—ability is most crucially determined by the time-difference between the sounds arrival to the left and right ears. Perception of distance is based on neural analysis of spectral cues, which thus comprises more complex handling.

One group of tests examines how the neural coding of auditory input is influenced by time, amplitude and frequency. These tests aim at the different underlying structures in the brain that handle the specific aspects of stimuli. Time analysis for example demands involvement from the brains feedback system in the frontal lobes; analysis of amplitude and modulation comprises mechanisms in different loci in the brainstem and coding of frequency is based on at least three different systems for detection. It is to be understood that modifications and alterations of said tests are possible while still being inside the scope of the present invention. Therefore, these tests are to be interpreted as examples of possible tests, and not to limit the scope of protection of the present invention in any way.

Thus, in one embodiment of the present invention one group of tests or one example of a test battery are/is provided according to the tests 1 to 9 below.

Test 1 "Forward Masking"

"Forward masking" (11) means the reduced ability to perceive one sound in the presence of another temporally preceding sound. In this test the stimuli consist of a Butterworth-filtered white noise (b fbw) which masks a subsequent square-shaped sound pulse (sssp).

Test 2 "Backward Masking"

"Backward masking" (12) means the reduced ability to perceive one sound in the presence of another temporally following sound. In this test the stimuli consist of a Butterworth-filtered white noise (b fbw) which masks a preceding square-shaped sound pulse (sssp).

Test 3 "Binaural Forward Masking"

"Binaural forward masking" (13) is characterized by the reduced ability to perceive a sound in one ear in the presence of another temporally preceding sound presented in the other ear. In this test the stimuli consist of a Butterworth-filtered white noise (b fbw) in one ear which masks a subsequent square-shaped sound pulse (sssp) in the other ear.

Test 4 "Directional Hearing"

In the test "Directional hearing" (14) square-shaped sound pulses (sssp) are presented in separate steps from left to right in equidistant angle-steps. This test consists of five subtests, each with its own specific angle (a-e). In the first subtest the sound originates completely from left (e). In subtest number two the pulse train are presented from an angle of 45° left (d). Subtest number three consists of a pulse train from the front (c). In the fourth subtest the pulse train are presented from 45° right (b) and finally subtest number five 90° right (a).

Test 5 "Perception of Distance in Sounds"

The test "Perception of distance in sounds" (15) consist of a number of subtests. In the first of these a pulse train consisting of square-shaped sound pulses (sssp) is used as stimulus (g). This subtest creates a reference value. In the second subtest (h) the square-shaped sound pulses have been altered through artificial treatment which makes them being perceived as originating from a distant location. In the following subtests the square-pulses in the pulse trains are even more modulated and thus are perceived as being more distantly located.

Test 6 "Pulse Train 1"

The test "Pulse train 1" (16) is comprised by a number of subtests. The subtests consists of pulse trains with specific time intervals (t isi) between the included square-shaped pulses (fp). In the first subtest the time interval has a constant value. In the other subtests the mentioned time interval is modified.

Test 7 "Pulse Train 2"

The test "Pulse train 2" (17) is comprised by a number of subtests. In the first subtest the included square-shaped pulses have specified constant amplitudes. For the other subtests this value is modified (a fp), and each subtests square-shaped pulses (fp) have their own specific constant amplitude.

Test 8 "Pulse Train 3"

The test "Pulse train 3" (18) is comprised by a number of subtests. In the first subtest the included square-shaped pulses have specified constant frequencies. For the other subtests this value is modified (f fp), and each subtests square-shaped pulses (fp) have their own specific constant frequency. The frequencies of the square-shaped pulses are obtained through filtering with a Butterworth-filter.

Test 9 "Pulse Train 4"

The test "Pulse train A" (19) is comprised by a number of subtests. In the first subtest the included square-shaped pulses have a specified constant duration. For the other subtests this value is modified (t fpd), and each subtests square-shaped pulses (fp) have their own specific constant duration.

The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims and description above, the term "comprises/comprising" does not exclude the presence of other elements or steps. Furthermore, although individually listed, a plurality of means, elements or method steps may be implemented. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A system for detection of brainstem disorders in a subject comprising:
    a sound stimuli generation device;
    a communication device delivering sound stimuli of said sound stimuli generation device to said subject;
    an analysis device adapted to record said subject's electrophysiological brainstem activity resulting from said sound stimuli;
    a triggering device connected to said sound stimuli generation device, said triggering device sending a triggering signal to said analysis device substantially simultaneously to the delivering of said sound stimuli to said subject;
    wherein said system further comprises a program and wherein said program causes said sound stimuli generation device to generate multiple sound stimuli tests.

2. The system according to claim 1, wherein said sound stimuli comprises a sound signal having varied properties in frequency, time and amplitude.

3. The system according to claim 1, further comprising an imaging instrument connected to said analysis device, said imaging device displaying said electrophysiological brainstem activity substantially simultaneously to the sending of said triggering signal to said analysis device.

4. The system according to claim 1, wherein said system is configured such that said analysis device records said subject's electrophysiological brainstem activity within a time span of approximately 0 to 10 ms after an initiation of said sound stimuli by said sound stimuli generation device.

5. The system according to claim 1, wherein each of said multiple sound stimuli tests comprises repeated sequences of a sound pattern.

6. The system according to claim 5, wherein each sound pattern is repeated approximately 500-1500 times and wherein the time between each of said repeated sound pattern is approximately 150 to 500 ms.

7. The system according to claim 1, wherein said sound stimuli is clearly differentiated in relation to other brainstem activity.

8. The system according to claim 1, wherein said system further comprises a program to compare said electrophysiological brainstem activity of said subject to standardized electrophysiological brainstem activity of a reference population such that the presence of brainstem disorder in the subject maybe detected.

9. The system according to claim 1, wherein said sound stimuli generation device comprises a tone generator.

10. The system according to claim 1, wherein said communication device comprises a hose or cord.

11. The system according to claim 1, further comprising memory recording and storing said subject's electrophysiological brainstem activity.

12. The system according to claim 1, wherein said multiple sound stimuli tests include at least the following:
    a forward masking test;
    a backward masking test;
    a binaural forward masking test;
    a directional hearing test;
    a perception of distance in sounds test;
    a pulse train 1 test;
    a pulse train 2 test;
    a pulse train 3 test;
    a pulse train 4 test.

13. The system according to claim 1, wherein said program is adapted to detect schizophrenia.

* * * * *

UNITED STATES PATENT AND TRADEMARK OFFICE
CERTIFICATE OF CORRECTION

| | | |
|---|---|---|
| PATENT NO. | : 8,292,823 B2 | Page 1 of 1 |
| APPLICATION NO. | : 11/759871 | |
| DATED | : October 23, 2012 | |
| INVENTOR(S) | : Olli Olsson et al. | |

It is certified that error appears in the above-identified patent and that said Letters Patent is hereby corrected as shown below:

On the title page, Item (22), "Filed: Jun. 7, 2007" should read --PCT Filed: Dec. 8, 2005--.

On the title page, after Item (22), insert the following:

--(86) PCT No.: PCT/SE2005/001877

§ 371 (c)(1),
(2), (4) Date: Aug. 28, 2007

(87) PCT Pub. No.: WO2006/062480

PCT Pub. Date: Jun. 15, 2006--.

On the title page, after Item (65), insert the following:

--(30) Foreign Application Priority Data
Dec. 8, 2004 (SE)................0402998-9--.

Signed and Sealed this
Second Day of December, 2014

Michelle K. Lee
*Deputy Director of the United States Patent and Trademark Office*